Figure 1:
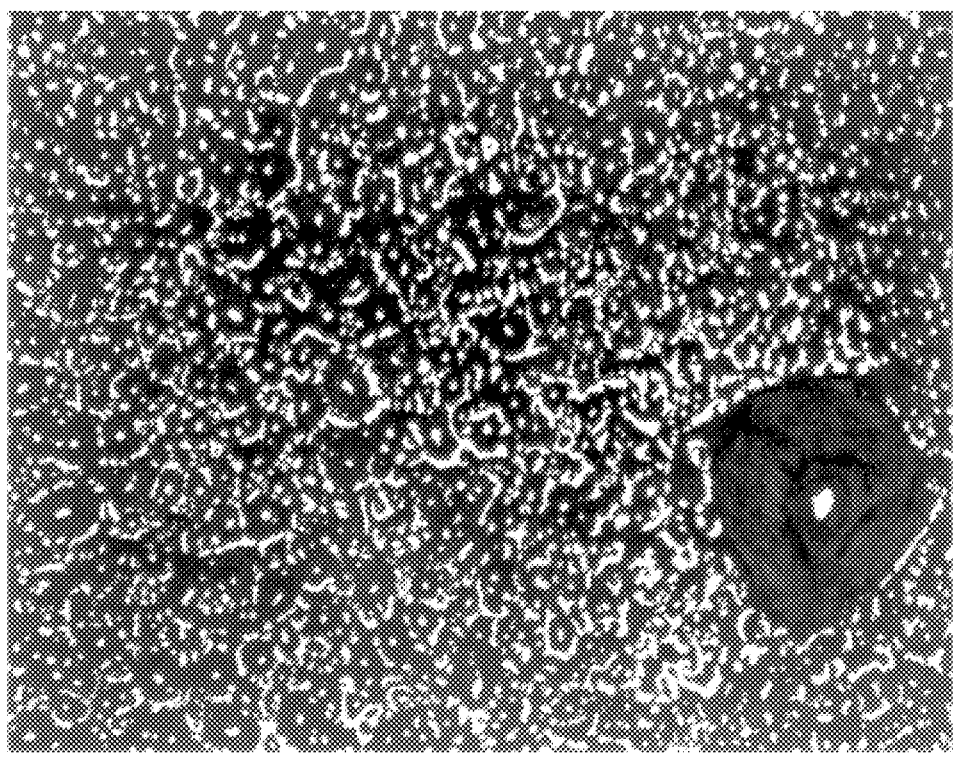

United States Patent [19]
Xu

[11] Patent Number: 5,817,322
[45] Date of Patent: Oct. 6, 1998

[54] PHARMACEUTICAL BASE AND THE USE OF THE SAME

[76] Inventor: Rongxiang Xu, 1-21-401 Fangguyuan, Fangzhuangxiaoqu, Beijing, China

[21] Appl. No.: 620,163

[22] Filed: Mar. 22, 1996

[30] Foreign Application Priority Data

Sep. 14, 1995 [CN] China .............................. 95 1 16651.4

[51] Int. Cl.⁶ ...................................................... A61K 7/48
[52] U.S. Cl. ........................ 424/401; 424/445; 424/484; 514/181; 514/182; 514/275; 514/365; 514/787; 514/887
[58] Field of Search ..................................... 424/401, 484, 424/445; 514/181, 164, 182, 275, 787, 887, 365, 95

[56] References Cited

U.S. PATENT DOCUMENTS

| | | |
|---|---|---|
| 3,761,590 | 9/1973 | Fox, Jr. ..................................... 424/228 |
| 4,101,652 | 7/1978 | Bonati ........................................ 424/49 |
| 4,279,901 | 7/1981 | Kudla ........................................ 424/241 |
| 4,623,667 | 11/1986 | Gans et al. ............................... 514/762 |
| 4,820,523 | 4/1989 | Shtohryn et al. ........................ 424/469 |
| 5,002,938 | 3/1991 | Wang et al. .............................. 514/171 |
| 5,011,680 | 4/1991 | Suzuki et al. .............................. 424/64 |
| 5,597,849 | 1/1997 | McGinity et al. ........................ 514/648 |

*Primary Examiner*—Jyothsan Venkat
*Attorney, Agent, or Firm*—Watson Cole Stevens Davis, P.L.L.C.

[57] ABSTRACT

The invention relates to the preparation and struction of a kind of pharmaceutical base comprising 5% to 25% by weight of beeswax and 95% to 75% by weight of a hydrophobic solvent. The pharmaceutical base has a netted framework structure with beeswax being the frame and the hydrophobic solvent being included in the frame. Also, the present invention relates to pharmaceutical compositions, dressing and cosmetics prepared by using the base and the method for preparing the same.

8 Claims, 1 Drawing Sheet

PHARMACEUTICAL BASE AND THE USE OF THE SAME

FIELD OF THE INVENTION

The invention relates to a pharmaceutical base and its use. More specifically, a kind of pharmaceutical base in the form of an ointment, with netted framework structure and the products manufactured using the base.

BACKGROUND OF THE INVENTION

An important route of the administration of drug for treating disease is external administration and the drug is absorbed through skin, mucous membrane or wound tissue. Nowadays, in the market, there are many kinds of pharmaceutical dosage forms to be used externally, but they have some disadvantages. For instance, ointments containing VASELINE as the base, when applied to the wounds, metabolic products and excreta from the wounds are not easily removed for the difficulty of passing through the base and to be drained away. The active drug dissolved in the base is difficult to pass through it to go into the wound tissue, so the efficacy of the drug is affected. Therefore, in physiological aspect, vaseline can not create an environment for promoting respiration of the wound tissue and it is not favorable to the normal respiration of the skin.

Besides VASELINE, pharmaceutical bases now in use include liquid paraffin, lanolin, beeswax, vegetable oil, glycerine monostearate, higher alcohols, polyethylene glycol and some emulsifying agents. Most of the commonly used pharmaceutical bases e.g. VASELINE, etc., do not have the effect of promoting drainage and protecting skin respiration.

DESCRIPTION OF THE INVENTION

To solve this problem, the present invention provides a kind of pharmaceutical base with characteristic netted framework structure and the method for preparing the same and products manufactured by using this base.

Beeswax has long been used as an excipient for manufacturing drugs for external use. In traditional Chinese medicine, beeswax is a drug for detoxication, granulation promotion, for relieving pain and cardialgia and treating diarrhea, pus and bloody stool, threatened abortion with vaginal bleeding, septicemia, refractory ulcer and thermal injury ("A Dictionary of Chinese Materia Medica", in Chinese, "Zhong Yao Da Ci Dian", Science and Technology Press, Shanghai, 1986, page 2581). Beeswax has wide application in manufacturing drugs for treating burns. For detail, see CN1090179A, CN1088800A and CN1098290A, etc.

The constituents of beeswax can be grouped into four categories, i.e., esters, free acids, free alcohols and paraffins. Beeswax also contains trace amount of essential oil and pigment. Among the esters, there are myricyl palmitate, myricyl cerotate, and myricyl hypogaeate. In free acids, there are cerotic acid, lignoceric acid, montanic acid, melissic acid, psyllic acid, hypogaeic acid and neocerotic acid. Among free alcohols, there are n-octacosanol and myricyl alcohol and in the paraffins, pentacosane, heptacosane, nonacosane and hentriacontane, and an olefin called melene. An aromatic substance called cerolein is also found in beeswax.

Since beeswax plays very important role in the formation of ointment and other dosage forms of drugs for external application, detailed research has been done through the following experiments by the inventor. The present invention is based on a detailed research on the property of beeswax and its interaction with hydrophobic solvents. The role and the action of beeswax in the pharmaceutical base of the kind are elucidated.

Heat beeswax to 60° to 70° C. just above its melting point, to make it a liquid. Heat the hydrophobic solvent which is usually an oily liquid at ambient temperature, to same temperature. Add an appropriate amount of beeswax (5% to 20% by weight based on the total amount of the base to be prepared) to preheated oily liquid. Allow the mixed liquid to cool spontaneously. While beeswax in the mixture is cooled to a temperature below its melting point, it gradually "crystallizes" to form a spongy substance. We can see under a microscope that the oil liquid has been included in the netted framework of beeswax. FIG. 1 is a micrograph taken at ambient temperature, using an infra-red microscope (CS1500–2000, Olympaus BH-2) magnified by 600 times. This inclusion is achieved by the formation of netted framework of beeswax.

Since beeswax is composed of esters, free acids, alcohols and paraffins, the framework can include hydrophobic subsances such as animal or vegetable oils as well as some hydrophilic substances. The method is well-known to the persons skilled in the art and is not necessary to describe here.

Our further research reveals that the netted framework structure of the pharmaceutical base forms a passable film after applied on body surface. Through the film, excreta and metabolic products from wounds can be drained away. Pharmaceutical base manufactured by using vaseline does not have this characteristic structure.

The object of the present invention is achieved by the following.

The present invention relates to a pharmaceutical base characterized in that it is composed of 5% to 25% by weight of beeswax and 95% to 75% by weight of a hydrophobic solvent, based on the total amount of said pharmaceutical base, and said pharmaceutical base has a netted framework structure, constituted by said beeseax, in which said hydrophobic solvent is included.

Among them, said hydrophobic solvent is usually an oily liquid, preferably a vegetable or an animal oil. The amount of the oily liquid is about 95% to 75%, preferably 93% to 80%, and more preferably 92% to 90% of the total weight of the base to be prepared.

The amount of beeswax in the base is usually 5% to 25% of the total weight of the base, preferably 7% to 20% and more preferably 8% to 10%.

The preparation of the pharmaceutical base with netted framework structure comprises the following steps:

heating beeswax to 60° to 70° C. or just above the melting point of the beeswax to make it a liquid;

heating a hydrophobic solvent to 60° to 180° C.;

adding the liquefied beeswax to the hydrophobic solvent in an amount that said beeswax will be 5 to 25%, and said hydrophobic solvent will be 95 to 75%, based on the total weight of the based prepared, and mixing thoroughly;

cooling the mixture spontaneously so that the netted framework of the base is formed, in which said hydrophobic solvent is included.

It is very important to have an appropriate proportion of the amount of beeswax to the amount of the hydrophobic solvent to ensure the formation of the netted framework and the inclusion. Otherwise, it is difficult to form the characteristic framework structure and the inclusion, we describe in this invention.

The pharmaceutical base of the present invention is suitable for manufacturing various ointments and creams for external use. The active drugs are preferably soluble in hydrophobic solvents such as oils. Preparing steps are following:

(1) heating the hydrophobic solvent containing the active drugs and stiring;

(2) heating beeswax to make it a liquid;

(3) adding the liquefied beeswax to the solution obtained from step (1), mixing thoroughly and cooling spontaneously to obtain a drug preparation, wherein, said hydrophobic solvent being usually an oil, especially a vegetable or an animal oil, in an amount of 95% to 75%, preferably 93 to 80%, more preferably 92 to 90% by weight based on the total amount of the base;

and, said beeswax being added in an amount of 5 to 25%, preferably 7 to 20% and more preferably 8 to 10%, based on the total amount of the base.

Said solvent is usually hydrophobic and is a liquid at ambient temperature, i.e., an oil and it may contain trace amount of water.

The active drugs may be a single drug or a mixture of drugs which can be dissolved in said solvent. Therefore, they are usually hydrophobic, such as antibiotics, sulfa drugs and β-sitosterol, etc.

Pharmaceutical compositions for external use manufactured using the base according to the present invention, when applied on the body surface of humans or animals (about 1 mm in thickness), adheres on the body surface. The netted framework composed of beeswax also gets into contact with the body surface and is warmed up. The solvent included in the framework begins to expand and the molecular movement becomes violent. As a result, the framework collapses and the included solvent containing active drugs is released. This process goes on continuously until the framework is completely collapsed and all the solvent released.

At the same time, excreta and other liquefied products from body also warmed up the framework and make it collapsed. Since the affinity of the solvent to the body surface is greater than that of the excreta, the excreta is rejected from the body surface to the outer part of the film.

Pharmaceutical compositions manufactured using the base according to the present invention have following advantages:

Firstly, it enhances the stability of the drugs and protects the drugs from contaminations. The netted framework of beeswax isolates the solvent to make it in form of particulates. The particulates do not contact each other. Beeswax has antioxidation and antibacterial effects and is resistant to alkali and water. Drugs dissolved in the isolated particulates are therefore protected from air, oxygen and other contaminations.

Secondly, it is unfavorable to the growth and proliferation of microorganisms but favorable to the control and prevention of infections. When microorganisms come into the particulates they are isolated by the framework and unable to proliferate or even to survive. So, the pharmaceutical base of this invention provides an environment unfavorable to the survival of microorganisms and therefore, controlling and prevention of infections are easily achieved. Pharmaceutical base of the present invention can be used to prepare ointments and creams and durgs of treating various diseases of the skin of different colors. Such as drugs of different dosage forms for external use, such as dressing, to be applied on ulceratd or not ulcerated skin, mucous membrane and sub-mucous tissue, for treating all kinds of mucous membrane erosions, traumatic wounds, wounds resulted from thermal injury, scarred skin due to different causes, skin contaminations and surface ulcers as well as ulcers of mucous membrane of hollow viscus. The pharmaceutical base according to the present invention can also be used to prepare cosmetics for beauty purpose by adding into skin care agents and perfume.

A BRIEF DESCRIPTION OF THE DRAWING

FIG. 1 is a micrograph showing the netted framework structure of the pharmaceutical base according to the present invention, prepared from beeswax and sesame oil according to the method described in example 1.

EXAMPLES

In the following, we are going to describe some examples and experiments in detail. This invention is not limited to these examples and experiments. Many variations will suggest themselves are within the full intended scope of the appended claims.

Example 1

Preparation of a Pharmaceutical Base with Netted Framework Structure

1. Materials

Beeswax

Putting honeycomb in water and heat to boiling. Collecting beeswax which it floats gradually on the surface of water. And then purifying it.

Sesame Oil

Purchasing sesame oil, which meets the international standard of food, from market.

2. Procedure

A. Heating 150 g of beeswax to its melting point and making it completely liquefied;

B. Heating 850 g of sesame oil to 180° C.;

C. Adding the liquefied beeswax into sesame oil at 180° C. Mixing thoroughly. Allowing to cool spontaneously. After cooling, the pharmaceutical base with netted framework was prepared.

FIG. 1 was a micrograph showing the net framework structure of beeswax and the inclusion of sesame oil, taken at ambient temperature, using an infra-red microscope CS1500–2000 (Olympaus BH-2), magnified by 600 times.

Example 2

Preparation of Ointment No. 1, Containing β-sitosterol Included in the Framework 1. Formulation

| | | |
|---|---|---|
| β-sitosterol | 5.5 g | (active drug) |
| beeswax | 80 g | (prepared as described in Example 1) |
| sesame oil | 920 g | (meets the International standard of food) |

2. Procedures

Heating sesame oil to 150° C. Adding β-sitosterol to the oil and mixing thoroughly until it completely dissolved. Heating beeswax to 70° C. Adding liquefied beeswax into the oil and stirring to cool down to 60° C. Allowing to cool spontaneously to form ointment No. 1.

Example 3

Preparation of Ointment No. 2, Containing β-sitosterol Included in the Framework 1. Formulation

| | | |
|---|---|---|
| β-sitosterol | 4.5 g | (active drug) |
| beeswax | 80 g | (prepared as described in Example 1) |
| rapeseed oil | 920 g | (meets the International standard of food) |

2. Procedure

Ointment No. 2 was prepared by the same procedure as described in Example 2, except for using rapeseed oil in place of sesame oil.

Example 4–6

Preparation of Ointment No. 3, 4 and 5 Containing β-sitosterol Included in the Framework The same procedure of Example 2 was repeated except that the amount of β-sitosterol in ointment No. 3 was 2 g, in oinment No. 4 was 4 g and in ointment No. 6 was 6 g, i.e., ointment No.3, 4 and 5 contained 2%, 4%, and 6% of β-sitosterol respectively.

Example 7

Preparation of Clotrimazole Ointment (No. 6)

1. Formulation

| | | |
|---|---|---|
| clotrimazole | 3 g | (active drug) |
| beeswax | 92 g | (prepared as described in Example 1) |
| sesame oil | 9 g | (meets the international standard of food) |

2. Procedure

Heating sesame oil to 150° C. Adding clotrimazole, mixing thoroughly to make it completely dissolved. Heating beeswax to 80° C. Adding the liquefied beeswax into the oil at 100° C., stirring well. Allowing to cool spontaneously. Clotrimazole ointment with framework structure was prepared.

Example 8

Preparation of Fluocinolone Acetonide Ointment (No. 7)

1. Formulation

| | | |
|---|---|---|
| fluocinolone acetonide | 0.25 g | (active drug) |
| beeswax | 200 g | (prepared as described in Example 1) |
| sunflower seed oil | 800 g | (meets the international standard of food) |

2. Procedure

Heating sunflower seed oil to 150° C., cooling for a while. Adding fluocinolone acetonide, mixing well to make it completely dissolved. Heating beeswax to 90° C. Adding the liquefied beeswax into the oil and stirring thoroughly. Allowing to cool spontaneously. Fluocinolone acetonide ointment with framework structure was prepared.

Example 9

Preparation of Sulfadiazine Silver Ointment (No. 8)

1. Formulation

| | | |
|---|---|---|
| sulfadiazine silver | 1 g | (active drug) |
| beeswax | 80 g | (prepared as described in Example 1) |
| sesame oil | 920 g | (meets the international standard of food) |

2. Procedure

The same procedure as described in Example 2 was repeated except for using sulfadiazine silver in place of β-sitosterol.

Experiment 1

Test of the Pharmaceutical Base on Body Surface

1. Design of the Experiment

Drew 3 circles on the dorsum of a hand. On circle A, vaseline was applied to a thickness of 1 mm and on circle B, the base was applied to a thickness of 1 mm. Circle C served as a blank control. Ambient temperature was 35°–40° C. Volunteers were allowed to drink 1 to 2 liters of boiled water until sweat appeared on the dorsum of their hands. Observation was made to see what happened in the skin in these 3 circles.

2. Result

In circle B, sweat passed through the pharmaceutical base with framework structure. In circle A, no sweat passed through vaseline film. The results were summarized in Table 1.

TABLE 1

| Circle | If there was liquid appeared on the skin? | Could the sweat pass through the oily film? |
|---|---|---|
| A | no liquid appeared | sweat could not pass |
| B | liquid appeared | sweat passed through |
| C | liquid appeared | sweat seen on the skin |

Experiment 2

A comparison between the efficacy of ointments prepared using pharmaceutical base of this invention and the typical base conventionally used as described in Chinese Pharcacopoeia.

A comparison was made between the efficacy of ointments (No. 6, 7 and 8) prepared in Example 7, 8 and 9, and that of ointments in market prepared by the methods described in the Chinese Pharcacopoeia. Total number of cases is 460. Table 2 showed the treating disease, curative rate, etc.

TABLE 2

| Drug | Ointment | disease | No. of cases | effective rate % | curative rate % | P value |
|---|---|---|---|---|---|---|
| Clotrimazole | commerical available | tinea pedis | 100 | 90 | 70 | |
| No. 6 (3%) | netted framework | tinea pedis | 100 | 96 | 94 | <0.05 |
| Fluocinilone | commerical available | tinea pedis | 100 | 92 | 65 | |
| No. 7 (0.025%) | netted framework | tinea pedis | 100 | 98 | 79 | <0.05 |
| | | | | effective for infection control | healing time of deep II burn wound | |
| SD-Ag | commerical available | burn | 30 | 91 | ×28 days | |
| No. 8 (1%) | netted framework | burn | 30 | 97 | ×21 days | <0.05 |

The results that the efficacy of the ointments prepared using the pharmaceutical base according to the present invention is better than that of the ointment prepared using conventional base.

What is claimed is:

1. A pharmaceutical base containing 5% to 25% by weight of beeswax and 95% to 75% by weight of a hydrophobic solvent selected from the group consisting of sesame oil, rape seed oil, and sunflower oil and an acceptable and effective amount of active drug where in the active drug is selected from the group consisting of β-sitosterol, sulfadiazine silver, clotrimazole and fluocinolone acetonide, and having a netted framework structure constituted by beeswax, in which the hydrophobic solvent being included.

2. A pharmaceutical base according to claim 1, wherein said hydrophobic solvent is sesame oil.

3. A method for preparing of a pharmaceutical base comprising following steps:
   (1) heating a hydrophobic solvent selected from the group consisting of sesame oil, rape seed oil, and sunflower oil and stirring it together with effective amount of active drug where in the active drug is selected from the group consisting of β-sitosterol, sulfadiazine silver, clotrimazole and fluocinolone acetonide;
   (2) heating beeswax to a temperature just above its melting point to make it a liquid;
   (3) adding the liquefied beeswax to the hydrophobic solvent at a temperature of 60° to 180° C. obtained in step (1) to an amount that beeswax is 5 to 25% by weight based on the total amount of the pharmaceutical base, and stirring thoroughly, then cooling it spontaneously, to obtain said pharmaceutical base.

4. A method according to claim 3, wherein said vegetable oil is sesame oil.

5. A pharmaceutical composition for external application prepared according to the method claimed in claim 3.

6. A drug for external application containing the pharmaceutical base according to claim 1.

7. A dressing containing the pharmaceutical base according to claim 1.

8. Cosmetic product containing the pharmaceutical base for external application according to claim 1.

* * * * *